(12) United States Patent
Göbel (10) Patent No.: US 9,119,697 B2
(45) Date of Patent: *Sep. 1, 2015

(54) DEVICE FOR SEALING AND DRAINAGE OF A NATURAL OR ARTIFICIAL INTESTINAL OUTLET

(71) Applicant: Advanced Medical Balloons GmbH, Frankfurt am Main (DE)

(72) Inventor: Fred Göbel, Wilhelmsfeld (DE)

(73) Assignee: Advanced Medical Balloons GmbH, Frankfurt am Main (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/974,613

(22) Filed: Aug. 23, 2013

(65) Prior Publication Data

US 2014/0163312 A1 Jun. 12, 2014

Related U.S. Application Data

(63) Continuation of application No. 12/932,702, filed on Mar. 3, 2011, now Pat. No. 8,529,429, which is a continuation-in-part of application No. 11/658,381, filed as application No. PCT/EP2005/007950 on Jul. 21, 2005, now abandoned.

(30) Foreign Application Priority Data

Feb. 9, 2005 (DE) .......................... 10 2005 005 988
Apr. 15, 2005 (DE) .......................... 10 2005 017 652
May 6, 2005 (DE) .......................... 10 2005 021 081

(51) Int. Cl.
*A61F 2/02* (2006.01)
*A61F 2/00* (2006.01)
*A61M 25/10* (2013.01)

(52) U.S. Cl.
CPC .......... *A61F 2/0013* (2013.01); *A61M 25/1002* (2013.01); *A61M 25/1018* (2013.01);
(Continued)

(58) Field of Classification Search
CPC ... A61F 2/0004; A61F 2/0009; A61F 2/0013; A61F 2/0027; A61F 5/445; A61M 25/1006; A61M 2025/1065
USPC ........ 600/29–32, 37; 604/327, 328, 332, 335, 604/337, 338
See application file for complete search history.

(56) References Cited

U.S. PATENT DOCUMENTS

3,447,533 A 6/1969 Spicer
3,802,418 A 4/1974 Clayton
(Continued)

*Primary Examiner* — Charles A Marmor, II
*Assistant Examiner* — Carrie R Dorna
(74) *Attorney, Agent, or Firm* — Panadiscio & Panadiscio (57) ABSTRACT

The invention relates to a device for sealing and draining an intestinal outlet, the device comprising an inflatable balloon of a generally toroidal structure, whose two ends extend one inside the other, creating a sealed-off volume inside the balloon, whereby the filling of the volume can be adjusted from outside and a draining lumen radially inside the inner layer of the balloon, the outer layer of the tube comprising a radially expanded intra-rectal device which is placed inside the rectum or the intestine of a patient during use, and comprising a trans-anal device which extends through the anus of the patient or his abdominal wall, and a stiffening sleeve element positioned inside the draining lumen of the device, keeping the lumen open and facilitating the uptake and passage of feces through the intra-rectal segment of the draining lumen.

29 Claims, 6 Drawing Sheets

(52) U.S. Cl.
CPC .... *A61M25/1027* (2013.01); *A61M 2025/1052* (2013.01); *A61M 2025/1065* (2013.01); *A61M 2210/1067* (2013.01)

(56) References Cited

U.S. PATENT DOCUMENTS

| | | | |
|---|---|---|---|
| 4,241,735 A | 12/1980 | Chernov | |
| 4,258,704 A | 3/1981 | Hill | |
| 4,344,434 A | 8/1982 | Robertson | |
| 4,555,242 A * | 11/1985 | Saudagar | 604/103.08 |
| 4,686,985 A | 8/1987 | Lottick | |
| 4,850,953 A | 7/1989 | Haber et al. | |
| 5,545,179 A * | 8/1996 | Williamson, IV | 606/213 |
| 5,569,216 A | 10/1996 | Kim | |
| 6,033,390 A | 3/2000 | von Dyck | |
| 6,527,755 B1 | 3/2003 | Salama | |
| 6,605,055 B1 | 8/2003 | Sinofsky et al. | |
| 2004/0044307 A1 | 3/2004 | Richardson et al. | |

\* cited by examiner

DEVICE FOR SEALING AND DRAINAGE OF A NATURAL OR ARTIFICIAL INTESTINAL OUTLET

REFERENCE TO PENDING PRIOR PATENT APPLICATIONS

This patent application is a continuation of pending prior U.S. patent application Ser. No. 12/932,702, filed Mar. 3, 2011 by Fred Göbel for DEVICE FOR SEALING AND DRAINAGE OF A NATURAL OR ARTIFICIAL INTESTINAL OUTLET, which in turn is a continuation-in-part of prior U.S. patent application Ser. No. 11/658,381, filed Oct. 21, 2008 by Fred Göbel for DEVICE FOR CLOSING A NATURAL OR ARTIFICIAL ANUS, which patent application in turn claims benefit of:

(i) International (PCT) Patent Application No. PCT/EP2005/007950, filed 21 Jul. 2005;

(ii) German Patent Application No. 10 2005 021 081.3, filed 6 May 2005;

(iii) German Patent Application No. 10 2005 017 652.6, filed 15 Apr. 2005;

(iv) German Patent Application No. 10 2005 988.0, filed 9 Feb. 2005; and (v) International (PCT) Patent Application PCT/EP2004/008256, filed 23 Jul. 2004.

The above-identified patent applications are hereby incorporated herein by reference.

BACKGROUND OF THE INVENTION

1. Field of the Invention

The invention relates to a device for sealing and draining of a natural or artificial intestinal outlet, the device comprising an inflatable balloon with a generally toroidal structure.

2. Description of the Prior Art

U.S. Pat. No. 3,802,418 discloses a colon catheter for indwelling removal of feces. The device comprises a ring-like balloon structure fixed on a distal end of a separate continuous trans-anal shaft element. The balloon structure comprises an elastic, latex like, material which is distended to a ring shape by a required filling pressure. A portion of the device extending through the anus is not a part of the balloon, but a shaft element inserted into the toroidal balloon and extending through the anus to the outside. Therefore, the trans-anal and intra-rectal portion of such shaft element is sufficiently rigid in consistency to keep the drainage lumen open and withstand the lumen-collapsing effect of the elastically expanding anchoring intra-rectal balloon element. Such devices are known to cause trauma in several regards, during prolonged placement in the body. The rigid trans-anal catheter shaft typically causes mechanical irritation and ulcers of the anal mucosa. Further, its continuous anal placement causes a permanent dilation of the anal sphincter, which may influence the function of the sphincter muscle after removal of the device. The intra-rectal catheter balloon, on the other hand, often induces the formation of pressure associated ulcers in the terminal rectum, due to the pressured, solid consistency of the anchor balloon.

In U.S. Pat. No. 5,569,216 a more advanced catheter for prolonged rectal placement is shown. The anchoring intra-rectal balloon is a thin-walled elastic material. The trans-anal single-walled tube segment is elastic and expands to a required diameter during the passage of stool. It retracts to a smaller resting diameter afterwards. Due to the elastic and deformable nature of the trans-anal segment of the device, pressure and irritation related damage of the anal channel can be reduced. Further, the device is equipped with an intra-rectal occlusion function, sealing the intra-rectal portion of the drainage channel against feces and irrigation fluid. The device, though, does not grant an occlusion of the trans-anal passageway, nor can the trans-anal portion be expanded against the structures of the anal channel.

US 2004/0039348A1 is an improved continuation of U.S. Pat. No. 5,569,216, whereby the trans-anal and intra-rectal segment are each defined by their material hardness, whereby the most critical segment for non-traumatic long-term placement, the trans-anal device portion, is of a softer material than the less soft anchoring components of the head unit. The soft and pliable trans-anal tube segment comprises a single layer of silicone typical elasticity. An active seal, or opening, function of the trans-anal segment is not within the scope of US 200410039348A1.

In U.S. Pat. No. 5,545,179 (Williamson), there is described a device characterized by an inverted balloon body for use in laparoscopic procedures. The device provides a permanent gas tight seal "preventing the escape of pressurized carbon dioxide from the body cavity". Through the collapsed inner opening of the described toroid, surgical instruments can be inserted and withdrawn, and an air-tight seal against the introduced shaft of the instrument provided. The laparoscopic device contains a seal element, which "upon inflation . . . compresses the inner channel and the passage way it defines." The elastomeric sealing element "is preferably a unitary construction composed of an elastomeric material such as silicone", manufactured preferably in a dipping process over a mandrel. It comprises a funnel-like element at its proximal end outside the body, easing the insertion of an instrument through the tightly compressed inner channel, from the outside to the inside.

The device is adapted for short term usage, during a period of surgery, and is then removed. It is neither compatible with the requirements of atraumatic long-term placement, nor is it designed for trans-anal drainage of feces, or any other material, from the inside of the abdomen to the outside of the body. The force required to inflate the sealing toroid from an elastic base figure would occlude the drainage channel, and the passage of stool would be impossible. The uptake of liquid, and semi-liquid, feces by a funnel-like distal mouth-piece within the toroid, and the continuous flow, or passage, of bowel contents from the inside to the outside of the body through a completely preshaped, largely un-elastic, un-pressured balloon body is not an integral part of the former invention.

Williamson prefers a silicone elastomer. In order to reduce silicone typical friction in the open center when a surgical device is inserted or withdrawn. The inner channel of the toroid can be optionally co-molded with polyethylene or polyurethane.

In U.S. Pat. No. 4,555,242 (Saudagar) there is described a drainage device, which is inserted into a surgical stoma through the abdominal wall. The device employs a unique construction of the balloon, which is based on a highly compliant, silicone-like elastomer with a typical elongation of 600 to 900 percent.

The elastic, partially preshaped balloon element is mounted on a flexible, but non-collapsible shaft element, providing continuous drainage of urine through the shaft lumen, when the balloon on its outside is expanded by inflation to seal pressure. The shaft element reaches from the distal device end inside the bladder cavity continuously to the proximal end outside the body wall.

The specific structural and compliance properties of the balloon enable a particular seal effect within the trans-abdominal channel, and an anchoring function against the bladder wall. The device includes a partially shaped balloon element, which is distended to its seal and anchor configuration in two distinct stages of balloon inflation. First, the tubular segment of the balloon begins to expand elastically within the trans-abdominal stoma; second, the distal bulbous end expands inside the bladder. In order to secure the initial distension of the tubular segment, its wall thickness is sufficiently thinner than in the bulbous intra-abdominal anchor segment.

The device is designed to "drain directly through a stoma, rather than through the urinary sphincter and the urethra", for placement periods of up to two or three months. Due to its non-collapsible trans-abdominal portion, it cannot be placed inside a sphincter muscle without causing tissue irritation, and other sphincter trauma, related to permanent dilation of the anal opening and the muscle.

SUMMARY OF THE INVENTION

The object of the present invention is to provide a device of the aforesaid type for sealing and draining a natural or artificial intestinal outlet, such that intermittent or continuous emptying of the bowel is feasible without removing the intestinal seal, and tissue irritation and damage, which is usually associated with continuous placement of a device of state of the art design inside the terminal rectum and the trans-anal channel, is reduced to a minimum.

To solve this problem, the invention provides a device for sealing and draining a natural or artificial intestinal outlet, the device comprising an inflatable balloon with a generally toroidal structure, formed of a flat, everted tube segment the two ends of which extend generally coaxially one inside the other and are each connected with their ends to a sleeve, preferably a common sleeve, creating a sealed-off volume inside the balloon, whereby the filling of the volume is configured to be adjusted from outside of the body, and creating a draining lumen radially inside the inner layer of the everted balloon, the outer layer of the everted tube segment comprising a radially expanded intra-rectal device portion which is placed inside the rectum, or the intestine, of a patient during use, and comprising a trans-anal device portion narrowed with respect thereto, which extends through the anus of the patient, or his abdominal wall, during use, whereby a stiffening sleeve element is positioned inside the draining lumen of the intra-rectal device portion, keeping the lumen open and facilitating the uptake and passage of feces through the intra-rectal segment of the draining lumen, while the two concentric tube layers of the trans-anal device portion, depending on the filling status of the sealed-off volume, can either be collapsed inside the anal channel to a small diameter, thereby forming a non-dilating structure, but allowing for free spontaneous passage of feces, or can unfold and erect inside the anal channel, thereby forming a trans-anally sealing structure with occluded drainage lumen.

The everted balloon structure includes a toroidal intra-rectal device portion, as well as a trans-anal concentric arrangement of the tubular balloon ends of the toroid. The everted balloon is provided with two volume sections, wherein one volume section is defined by the intra-rectal torus, and the other by the space between the two concentric trans-anal tube segments. The volume sections are in free communication with each other. During use, the intra-rectal device portion is placed inside the intestine of the patient, especially in the rectum, in case of a natural intestinal outlet. On the other hand, during use, the trans-anal device portion extends through the anus, or through an opening in the patient's abdominal wall. During use, both ends of the tube everted to form the balloon are seated outside the patient, that is, outside the anus and the abdominal wall. For this reason, a device for sealing an artificial intestinal outlet is distinguished into intra-intestinal device portion instead of intra-rectal device portion on the one hand, and into trans-abdominal device portion, instead of trans-anal device portion on the other hand. In the following, as well as in the accompanying claims, the term "intra-rectal device portion" shall mean "intra-intestinal device portion" in case of a device for sealing an artificial intestinal outlet, and in the same case, "trans-anal device portion" shall mean "trans-abdominal device portion".

Furthermore, the everted balloon provides an open central channel in its center, enabling the passage and drainage of bowel contents through the anus into a connected receptacle.

The balloon body is fabricated to the dimensions of its working state and does not require to be stretched up or distended by force, in order to fulfill its anchoring, sealing, and draining function, in the body. Therefore, as the balloon wall is not stretched, or otherwise elastically deformed, it exerts no restoring force. For this reason, it does not produce any additional pressure inside the balloon, and the pressure inside the balloon is equal to the pressure outside the balloon. For this reason, no excess pressure exceeding the pressure within the adjacent body tissue is developed, and therefore, the rectum and anus will not suffer any injuries, traumata, or the like.

During use, preferably a liquid is filled into the sealed-off volume inside the balloon. The entire volume of the liquid filled into the balloon volume is less than the volume of the balloon at its free unfolded state, so that the wall of the balloon is not stretched.

Depending on the filling volume, which is applied into the balloon, the inner tubular balloon segment of the two concentric trans-anal tube layers can be either collapsed or compressed to a tightly sealing structure, then actively occluding the central drainage channel, or it can be kept in a passively collapsed condition inside the anal channel without entirely sealing the central opening, but allowing for feces to pass through the central opening spontaneously. The uptake of feces inside the rectum is facilitated by a stiffening funnel-like sleeve element, which is positioned in the central lumen of the intra-rectal portion of the everted balloon. This sleeve element keeps the distal entry section of the drainage channel open and guides the feces through the rectally anchoring toroid directly to the anal sphincter. In contrast to the continuously open toroidal section of the drainage channel, the passage of feces through the trans-anal portion of the drainage is adapted to be actively adjusted, and set, by care personnel. The invention further provides various means for determining the elastic collapse and self-erection capabilities of the trans-anal device portion, easing the passage of feces through the anal channel.

In the present invention, the trans-anal/trans-abdominal portion is fully collapsible, is made at its outside and inside of a flexible tube foil arranged in a double concentric layer. The drainage lumen is not permanently open, but compressed and occluded by the sphincter, which is resting thereon. Any permanent distension of the sphincter muscle, and associated harmful effect, can thus be largely prevented.

Unlike Saudagar, the portion of the device presented herein that is passing through the abdominal wall, or the anal sphincter, is of a material, preferably thicker-walled than the distal bulbous portion, in order to decrease the likeliness of torsion of the trans-anal drainage channel. The design presented herein alleviates the problem of permanent occlusion by torsion, by a careful combination of wall-thickness and material elasticity, as well as additional structural modifications of this particular function critical device portion. In contrast to Saudagar, the wall-thickness of the distal intra-cavity portion of the present invention is preferably lower than in the proximal portion, in order to provide the best possible adaption to the individual situs of the terminal rectum, at an incompletely filled and saggy condition of the toroidal balloon body.

Unlike Saugadar, the balloon is of a material of low compliance, which is fully shaped to its working state dimension, and does not require to be distended under potentially harmful filling pressures. Due to the gained polymeric orientation during the blow-molding procedure, balloon foils can be made, which are very thin-walled, durable, and have limited compliance. The limited compliance means that when a pull force is applied on the device from the outside, the pressure inside the (preferably incompletely) filled balloon rises according to the force acting thereon; the shape of the toroid is stable and keeps the device reliably anchored. Elastic deformation and slipping of the device out of the anus can be prevented.

It is within the scope of the invention that the material hardness H1, determinable according to the Shore A hardness test, of the tube segments in the trans-anal region is greater than 70, preferably greater than 80, so that on the one hand production of raw-tubing is possible by conventional extrusion, and on the other hand, the expansion and deformation that occurs when the balloon is inflated, or exposed to external force, is predictable and limited in extent.

The wall-thickness of the balloon, in the region of its outer layer, should be less than 80 μm, preferably less than 50 μm, ideally less than 30 μm.

The material thickness of the intra-rectal toroidal expansion of the everted balloon ranges from 50 to 20 μm, preferably from 30 to 20 μm, and the thickness of the individual tube segments of the trans-anal device portion ranges from 200 to 30 μm, preferably 60 to 40 μm.

This makes for sufficient pliability, despite the relatively high material hardness H1, so that this region can be collapsed to a minimally low cross section, and grants in combination with the thus gained soft-foil aspect of the everted balloon, a low degree irritation of the exposed rectal and anal tissue.

The invention preferably is of polyurethane (PUR) for a tube segment forming the balloon. PUR based, or similar materials, provide the required hardness range and can be preshaped to complex foil bodies; furthermore, the tube segment forming the balloon can be fabricated with a very thin wall thickness, showing high mechanical durability, tissue friendly soft-foil properties, and a limited compliance when being pressurized, or exerted to a pull force.

It has proven effective for the stiffening sleeve to have a material hardness H2 determinable according to the shore A hardness test that is equal to or less than, the material hardness H1 determinable to the Shore A hardness test of the tube segments in the trans-anal region. Since the stiffening sleeve is fashioned as significantly thicker than the balloon, and has to remain inside the rectum of a patient along with the toroidal balloon as many as thirty days or more, it must not be too hard, to avoid irritating or even injuring the intestinal mucosa. This is achieved by a limited hardness H2 for the sleeve material. One preferred option is to make the tube and the stiffening sleeve of the same material, reducing material costs and easing bonding.

It has also proven favorable for the material hardness H2 and the wall thickness of the stiffening sleeve to be selected such that the lumen opening sleeve elements can be compressed radially to facilitate the trans-anal insertion of the device into the rectum. These two parameters affect the actual hardness and pliability of the stiffening sleeve.

This means that the harder the material of the stiffening sleeve, the thinner-walled the sleeve must be, and vice versa.

Instead of a sleeve element, an annular, cylindrical, or funnel-shaped, foam structure can be used as a lumen opening structure inside the toroidal section of the drainage channel. The foam structure can be a voluminous spherically, or cylindrically, shaped body with a relatively large diameter, providing a certain intra-rectal anchoring function. The foam is sufficiently soft to be compressed for trans-anal insertion and withdrawal, yet has an elasticity that grants sufficient re-erection after deformation during insertion. When being positioned inside the drainage channel and exposed to feces, the surface of the foam body is preferably coated with a thin layer of sealing material, or it is manufactured in a fashion that the surface is sealed and does not soak up intestinal secretions.

The stiffening sleeve element is adapted to be positioned within the open central lumen of the toroidal intra-rectal section of the balloon in such fashion as to be completely separated from the hollow space inside the balloon by the continuous inner layer thereof. Alternatively, the sleeve element is adapted to be positioned inside the toroid, in the space created between the outer and inner walls of the everted balloon structure, thus being protected from exposure to feces. The positioning of the sleeve in the inside of the toroidal balloon is favorable when foam based funnel elements are used.

The stiffening funnel element (sleeve) should not be connected to either end of the tube segment forming the balloon, so that relative movements between the stiffening sleeve and the further proximal portions of the device outside the patient can take place such that the intra- and extracorporeal portions of the device can be largely mechanically decoupled.

This inventive idea can be developed alternatively by having both ends of the tube segment forming balloon disposed beyond the trans-anal region (outside or remote from the patient). In the preferred case, both ends of the (single) tube segment are disposed outside the rectum and anus, so that over the entire length of the anal channel a sealing radial expansion of the trans-anal device portion and the largest possible contact area between device and anus is created.

A sleeve connected to at least one end of the tube segment forming the balloon is preferably configured as an extracorporeal connector element. Various instruments, devices, or other functional elements, can be connected thereto; for example, gas permeable occlusion elements, flushing devices, or as in the present invention, draining tube elements leading to a receptacle remote from the patient.

The fact that the sealed-off volume inside the balloon can be regulated from the outside makes it possible to deliberately influence the geometry of the draining passageway in the center of the everted balloon structure, thus adjusting the draining channel, either for primary seal, or primary drainage. Furthermore, the trans-anal passageway provided by the device does not include a shaft element, or the like. It consists of only two roughly concentric layers of tubular foil, which can be easily collapsed to a structure of very low diameter by the anal structures resting thereon. Accordingly, typical tube/shaft placement associated irritation, or damage, of the anus is largely prevented.

The balloon material is preferably of limited compliance, preventing the anchoring intra-rectal toroid from being elastically deformed to such a degree that it loses its anchoring shape and may slip through the anal opening.

After insertion of the device into the body, the balloon can be filled with a filling volume, which is about equivalent to the spatial volume defined by the freely unfolded torus section plus the spatial volume of the freely unfolded outer trans-anal tube segment. In that particular filling condition, the inner trans-anal tube segment is actively collapsed, and the drainage lumen tightly occluded (active lumen occlusion), while the outer trans-anal tube segment is actively moved against the structures of the anal channel (active anal seal).

In order to allow a continuous passage of bowel contents through the everted balloon structure (continuous drainage), the applied filling volume of the balloon can be reduced to a volume which accords the spatial volume for active occlusion, minus the spatial volume of the freely unfolded outer trans-anal tube segment.

In order to allow for the lowest possible filling pressure, and to prevent a potentially harmful effect of the inflated balloon on the exposed tissues, the balloon, in either filling condition (drainage and occlusion), is preferably filled only incompletely, with a volume that is about 10 to 20% smaller than the figured spatial filling volume of the freely unfolded everted balloon. This results in a flaccid balloon structure, whereby the toroidal portion is resting on the rectal bottom at nearly even force exertion on the balloon exposed structures. In the state of incomplete filling, the trans-anal portion of the flaccid balloon is snugly adjusting to the anal channel, whereby the concentric tube segments in the trans-anal portion are largely collapsed, fitting the actual anal opening. Only when an intermittent tight seal, or occlusion, is required, as, for example, during and after the installation of colo-rectal irrigation fluid, the applied filling volume should be equal to, or exceeding, the figured spatial occlusion volume. The filling volume is preferably applied and controlled by a syringe with volume markings thereon.

While the transport of feces into the distal funnel element, and further, through the central opening, of the everted balloon is driven by colo-rectal peristalsis, and the device is passively responding to the stool transporting forces, in an alternative embodiment of the invention, the trans-anal portion of the drainage channel is actively opening and unwinding under colorectal contraction. The described performance is enabled by a punctual, linear or areal connection between the outer and the inner tube of the concentric trans-anal balloon ends, by e.g., welding or gluing. The "active" opening and unwinding of the passageway will be explained further herein below.

Alternative to an occlusion of the drainage channel between a state of continuous drainage and intermittent tight seal by regulation of the balloon filling volume, the passage of feces can be controlled by at least one separate occluding balloon element, which unfolds or expands inside the drainage lumen. The occluding balloon is preferably positioned inside the stiffening sleeve, where, when deflated, it frees up the passage of feces. The balloon element can be made of a thin-walled, preshaped material. The shape of the occluding balloon, when inflated, can thus be specified fairly exactly, and the pressure needed to unfold the balloon can be kept relatively low, since it need not cause an elastic expansion of the balloon material.

Within an alternative embodiment of the invention, the occluding balloon can be formed by a fully elastically restorable compartment, which in the preferred case reaches from the distal end to the proximal end of the drainage channel in the center of the everted balloon.

The occluding balloon element is filled via a separate filling line from the outside.

It is advantageous to provide in the anterior region of the balloon, particularly in the region of the stiffening sleeve, a flushing opening connected to a conduit that extends along the trans-anal segment and serves to introduce a flushing or irrigation fluid.

The invention further describes radial expansions in the outer tube of the trans-anal device portion. The expansions are preferably integrated in embodiments of the invention which have a structural connection between the outer and inner tube segment of the trans-anal segment. The expansion is adapted to serve as a counter-element to the balloon-shaped extension in the intra-rectal tube segment. Its function is to keep the device in a defined position and prevent the dislocation of the anchoring and sealing intra-rectal balloon segment into the colon. In an advantageous improvement of the invention, the outwardly directed pre-shape in the trans-anal region of the outer layer of the balloon is provided with a ring or a disk shaped geometry. It is also possible for the outwardly oriented pre-shape to include one or more fingers that diverge roughly diametrically from each other. These finger-like extensions can be placed in the anal fold to maximize wearing comfort. A wedge shaped element can further be provided, particularly fastened over the outer layer of the tube segment forming the balloon, in the trans-anal region, or in the region of the transition from the trans-anal region to the connector element. A foam element of this kind can also serve as an abutment and, additionally, has increased rigidity, accompanied as a result by good positional stability.

As the device is to be placed over prolonged periods of time, pressure or force associated irritation of the mucosae and the skin have to be prevented. Therefore, an additional outer, very thin-walled tube foil layer can be part of the design, serving as a protective cover of the device exposed surfaces.

BRIEF DESCRIPTION OF THE DRAWINGS

The invention is explained in greater detail below with reference to exemplary embodiments.

In the drawings.

DESCRIPTION OF THE PREFERRED EMBODIMENTS

Figure 1A:
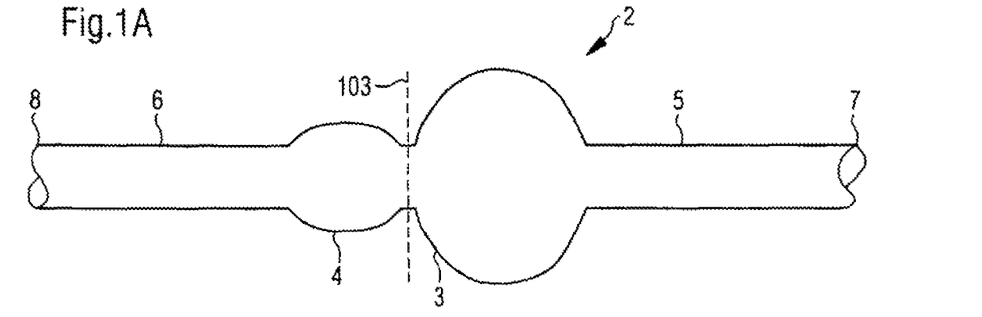
FIG. 1A is a schematic view of a non-everted pre-shaped tube.
Figure 1B:
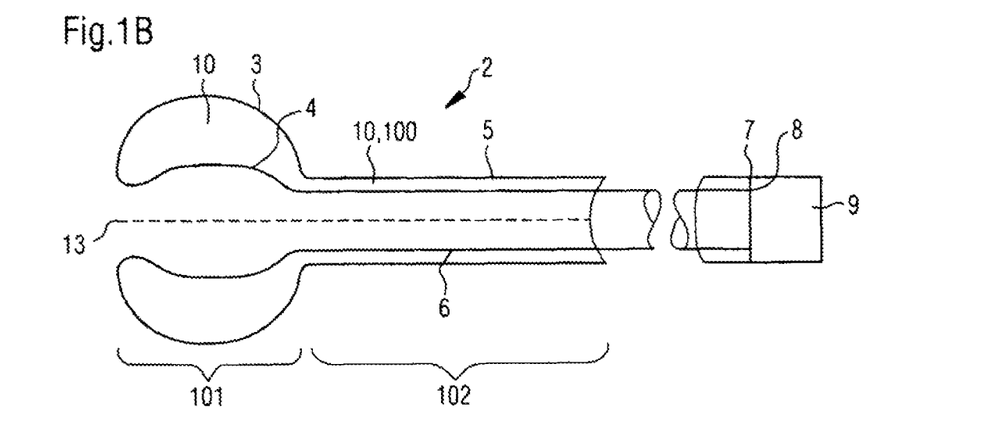
FIG. 1B is a schematic view of an everted pre-shaped tube.
Figure 1C:
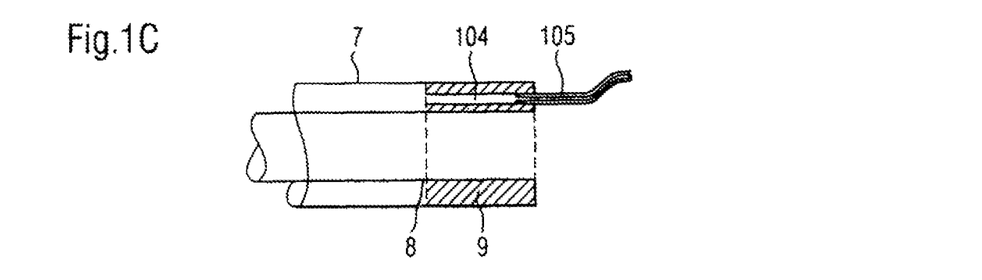
FIG. 1C is a schematic view of a proximal end of the trans-anal device portion of FIG. 1B.

The inventive device according to FIGS. 1A-1C serves to seal and drain a natural or artificial intestinal outlet. The device includes a preshaped and everted tube 2, made of a thin-walled and durable material of low compliance, for example polyurethane with a Shore A hardness of 90.

A non-everted example of the shaped tube 2 is shown in FIG. 1A. The tube 2 is provided with a spherical, elliptical or disk-shaped expansion 3 with two tube-like ends 5 and 6 at its sides, whereby the diameter of both tube ends are selected such that when everted (reverse folded), as shown in FIG. 1B, the tube ends fit into each other concentrically, creating a gap 100 of about 1 to 5 mm, preferably 1 to 3 mm in therebetween.

In the everted toroidal state, the shaped expansion 3 is provided with a diameter of 5 to 8 cm, preferably 5 to 7 cm. Its length in the everted state is between 2 and 6 cm, preferably between 3 and 5 cm. The toroidal balloon structure represents an intra-rectal portion 101 of the seal and drainage device.

The tube-like ends (5, 6) of the expansion 3 form an everted balloon in a coaxial arrangement, representing a trans-anal device portion 102. The trans-anal portion 102 is positioned inside the anal channel and adapted to drain the feces through the sphincter muscle to the outside. The length of the trans-anal portion 102 is typically of 8 to 15 cm. Its diameter on the outside is about 2.5 to 5 cm, preferably 3 to 4 cm.

The shaped tube 2 is everted to a toroidal balloon over a plane 103, as indicated in FIG. 1A.

Figure 3A:
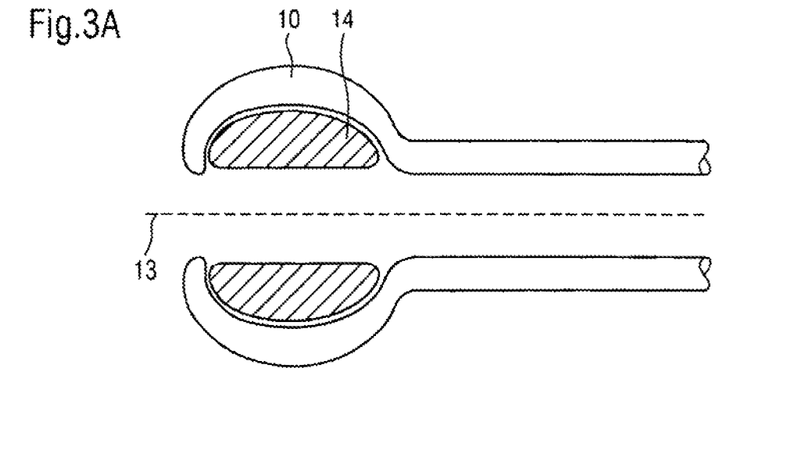
FIG. 3A shows a stiffening foam element placed inside a central opening of an intra-rectal portion of the device.
Figure 3B:
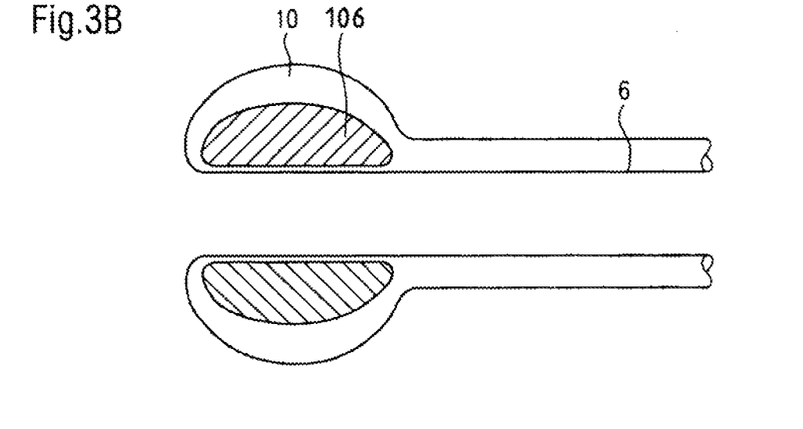
FIG. 3B shows a stiffening foam element positioned in the inside of the intra-rectal portion of the device.
Figure 3C:
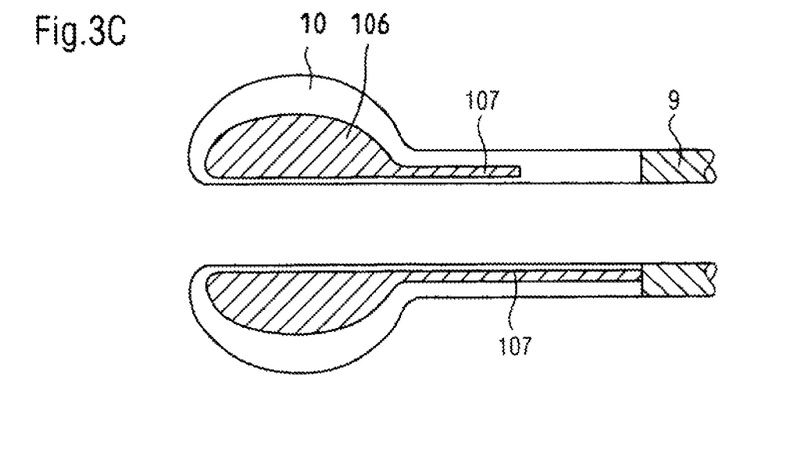
FIG. 3C shows a foam element according to FIG. 3B with a structural extension of a sleeve element into the trans-anal device portion.

Both free ends 7 and 8 of the two tube-like ends 5 and 6 are connected to a soft, flexible sleeve shaped connector element 9, as shown in FIG. 3C. A hollow space 10 between inner and outer layers of the tube (balloon) 2 is thereby sealed air-tight. The space 10 is pressurized via a filling channel 104, which is integrated into the connector element 9 and extended into the further proximal device portion by a connected filling hose 105.

In the region of the intra-rectal portion 101 of the everted tube 2, an inner lumen 13 is held open by a stiffening sleeve 14 whose length is preferably equal to, or less than, the axial extent of the intra-rectal expansion 3 of the tube 2. The material hardness of the stiffening sleeve 14 is preferably equal, to or less than, the material hardness of the tube (balloon) 2.

As pictured in FIG. 1A, a pouch-like expansion 4 can be shaped in the tube-like end segment 6, in order to provide a cavity for the insertion and placement of the stiffening sleeve element 14. In the inverted state, the cavity can take up a more voluminous, thicker-walled, e.g. foam based, sleeve in a fashion such that the sleeve body can be integrated into the inner lumen 13 of the drainage channel without narrowing the passage way for feces.

The preferred embodiment of the tube/balloon 2 is made from a single conventionally, or foil extruded, tube element of consistent quality and parameters.

Alternatively, balloons can be shaped from axially arrayed (welded, or glued) segments of tubing of specific hardness and/or thickness, thus granting a wide range of wall elasticity options of the individual device portions in the shaped final product.

The preferred shaping process is a conventional hot blow molding procedure, whereby the raw tube is stretched, then pressurized and blown into a mold cavity, heated and subsequently chilled.

As described in DE 10 2008 008 954.4 and DE 10 2010 008 577.4, the unshaped raw tube can be extended in length, in a way that it integrates the tubing element, which later in the assembled and finished product represents the extracorporeal portion of the device, draining the feces from the balloon 2 to a remote proximal collecting container. In that case, only the end section of the extended raw tube undergoes the molding process and receives the morphological details of the balloon 2, while the other end of the raw tube already has the required dimensions for its drainage function, or undergoes a process of "cold" deformation, whereby the draining tube section is maximally distended in a radial direction under pressure, without being heated, and then retracts incompletely to a larger, plastically deformed diameter, sufficient for efficient drainage. Either the inner or outer tube-like end 5 or 6 can be extended in length accordingly. By using such continuous, single pieces of raw tube, which are basically making up the entire passage way from the intra-rectal end to the collecting receptacle, material and manufacturing costs can be optimized. As shown in DE 10 2010 008 577.4, tubing material, which is made by a foil-extrusion process, permits the manufacturing of tubing material, which already has the required diameter and thickness requirements for the finished extracorporeal device portion, and is therefore the preferred raw material. Foil extrusion processes are economical and permit tubing dimensions, which cannot be extruded in polyurethane in a conventional extrusion process, and further allow multi-layer extrusion of up to five different material layers with individual, specifically chosen properties, serving as a vapor or odor barrier, layers containing antimicrobial agents, reinforcing layers improving the mechanical strength or modifying the material elasticity and its elastic self-erection capability.

The blow molded tube/balloon 2 is of a preferred thickness of about 25 µm in the expanded toroidal section 3. The corresponding thickness of the coaxially positioned tube-like ends 5 and 6 is about 30 to 100 µm. The thickness of the extracorporeal section of the draining tube is in the order of 300 to 1000 µm, preferably 400 to 600 µm.

Alternative to the described hot blow molding procedure, the tube/balloon 2, as well as the aforementioned optional extension of the extracorporeal draining section, can be made by a dipping procedure, whereby a mandrill is dipped into liquid polymer. The dipping process provides a uniform thickness in all dipped portions of the device, but also allows for thickness modification of individual segments by adding or lowering the number of dipping steps. For example, the thickness, and thus the flexibility, and/or elasticity, of the tube end 5, which forms the outer layer of the everted balloon, can be adjusted to equip the device with the appropriate elastic self erection properties, granting a collapse of the trans-anal device portion at the lowest possible sphincter force resting on it, as well as an immediate erection of the tube end and spontaneous opening of the drainage lumen, when the sphincter tonus lowers and the anus opens. Dipping can be performed on the basis of liquefied polyurethane, silicone, natural rubber, isoprenes, or blends of such materials. The balloon 2, in the dipped embodiment Of the invention, typically has a thickness of about 100 to 1000 µm, preferably 300 to 500 µm.

For all embodiments of the invention, the capability of the trans-anal device portion to collapse to a lumen closing structure at the lowest possible force, but also to erect spontaneously when the collapsing force (sphincter tonus) is decreasing, and/or the anal channel spontaneously opening, can be integrated into the design, facilitating the passage of feces though the intra-corporeal part of the drainage and out of the patient. The herein described trans-anal device portion should collapse at an collapsing force on the tubing outside from about 5 cm to 25 cm water column, preferably 5 to 10 cm. As a collapse of the drainage lumen in that context would be considered a state, where the circular acting collapsing force, which is exerted onto the outside surface of the trans-anal device portion, is bringing at least two diametrically positioned segments of the tubing into physical touch.

The tube/balloon 2 can be shaped with the second radial expansion 4. Expansion 4 is sized in length according to the length of the drainage channel within the everted intra-rectal portion of the device.

Because of its preferably higher material Shore hardness of about 80 A to 60 D, and therefore limited compliance, the everted and filled/pressurized balloon 2 behaves largely shape stable and undergoes only moderate elastic deformation. During intermittent pressure increase inside the balloon, as it may happen during controlled lumen occlusion or when an axially directed pull force is acting on the rectally positioned toroid from the outside of the patient, the preshaped balloon geometry remains largely consistent, preventing uncontrolled elastic deformation, or slipping of, the device through the anus out of the rectum, or through a trans-abdominal stoma out of the patient. The specific compliance restriction of the balloon allows for filling with a compressible gaseous medium, while anchoring balloons from silicone typical compliance, in order to decrease the likeliness of significant deformation and slipping, have to be filled with a non-compressible fluid.

Figure 1D:
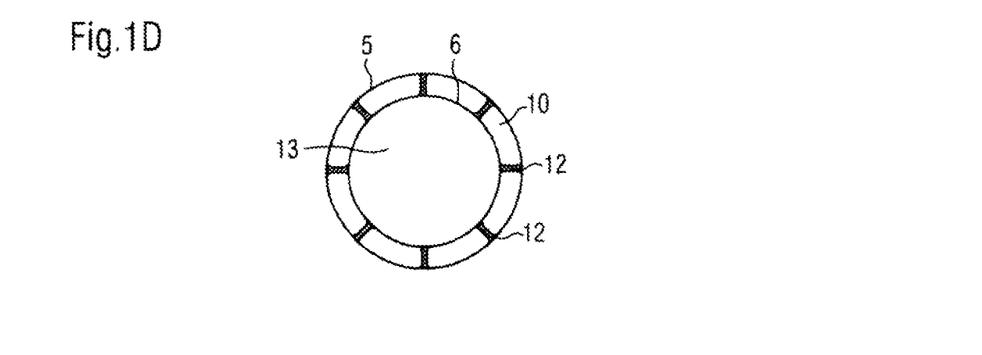
FIG. 1D is a schematic view of a cross-section of the trans-anal device portion, and tube structural connections between coaxial tube segments.
Figure 2:
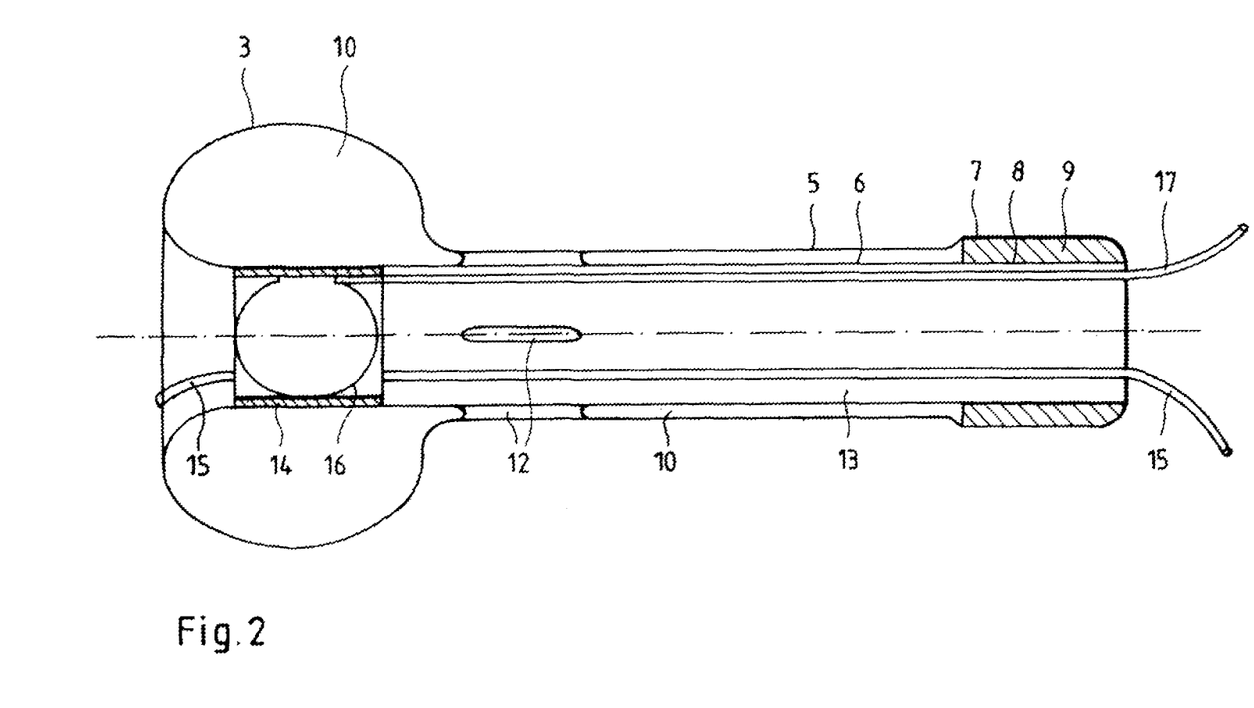
FIG. 2 is a schematic view of a longitudinal section through a first embodiment of the invention.

In another preferred embodiment, the two concentric tubes 5 and 6, making the trans-anal section of the everted balloon, are connected to each other, preferably by welds or adhesive bonds 12. These junctures can be punctiform, linear or areal. FIG. 1C shows a cross-section through the trans-anal device portion, picturing an example of eight structural connections (or bonds) 12 (FIG. 1D) of the tube ends, preferably extending in axial directions throughout the entire length of the trans-anal portion, each offset from the next by roughly equal circumferential angles. The number of the axially directed welds can be 4 to 12, preferably 5 to 10. By virtue of the bonds 12, the lumen of the inner tube segment 6 (the drainage lumen), can be actively supported in its opening by the sequential muscular contraction and relaxation taking place during defecation reflex.

Should a contraction of the rectal musculature occur during spontaneous emptying of the rectum, the resulting force is taken up by the intra-rectal balloon expansion portion 3, shifting its filling volume partially from the intra-rectal into the trans-anal portion of the space 10, and increasing the filling pressure within the space 10 to a roughly contraction equivalent level. The increase in pressure within the everted balloon element leads to straightening of the collapsed trans-anal device portion and causes an active opening of the central drainage lumen to its cross-sectional area. When being pressurized sufficiently, the outer tube segment 5 erects to its preshape and due to its surface larger than the surface of the inner tube, which is connected to it, takes the inner tube segment with it, thus opening the drainage lumen 13. The pneumatically supported opening of the draining lumen 13 of the trans-anal portion supports the spontaneous defecatory process.

An according active opening of the drainage lumen can also be initiated deliberately by the care personnel. For example, should a flushing of the bowel (enema) be performed, the filling pressure in the space 10 can be increased appropriately for the duration of the flushing procedure, and thus support the passage of colorectal content trough the trans-anal device portion out of the patient. Since in that pressurized condition the outer tube segment 5 is expanding against the anus and the drainage lumen in the inside opened, the removal of infused irrigation fluid and/or liquefied feces can be facilitated in a way that the risk of the bypassing feces along the device's outer surfaces into the bed can be minimized. This particular embodiment of the sealing and draining device is therefore ideally suited for controlled bowel management in the care of regular immobile home and hospitalized patients. A tube 15 preferably extends inside the lumen 13 front the connector element 9 to the inside surface of the stiffening sleeve 14. Through the tube 15, which can be affixed, for example by gluing, to the inner layer of the balloon 2, a flushing or irrigation medium can be infused into the bowel of the patient. In order to control and manage the rhythm of the defecation of a patient, intermittently irrigation volume can be installed in the rectum by the care personnel, triggering the defecation reflexes. With the onset of the colonic/rectal contractions, the bowel contents of the entire descending colon can be mobilized and egested. Thus, a defecation free period of about 24 hours and beyond can be reached.

A further advantage of the described movement of volume into the trans-anal portion and the associated pressure increase inside the space 10, is the active unwinding and de-torquing of the trans-anal segment, as in situ axial torsion of the trans-anal device portion may appear and impair the drainage efficacy of the device.

With the basic device embodiment, showing independently moving and non-interconnected coaxial tube-like 5 and 6, an occlusion of the drainage lumen 13 can be effected by filling the space 10 with a volume, which is sufficiently large to cause the inner tube end 6 to collapse to a tightly closing structure, sealing the drainage channel against the irrigation volume, being installed in front of the intra-rectal device portion, inside the rectum. The tube segment 5, on the other hand, expands under that specific filling volume against the structures of the anal channel, preventing the leaking of irrigation volume along the contact area between device and anus. The active anal seal provided by this basic device type allows to apply larger irrigation volumes, and to lock the irrigation fluid inside the colon when the peristaltic action has started, thus intensifying the trigger effect of the irrigation. In order to remove the colorectal contents, the filling volume in the space 10 is reduced to a volume which enables the drainage lumen 13 to open and the feces to be moved through the trans-anal passageway into the proximal draining tube portion.

The device embodiment with inter-connected coaxial tube layers, as shown in FIG. 1C, does not allow for an active seal during the instillation of irrigation fluid, instead provides a supporting effect on the outflow of the bowel content, when being inflated to a filling volume, causing the trans-anal device portion to erect circularly and thus to open the drainage lumen. The outer tube-like end 5 is then unfolding against the anal channel, while the intra-rectal toroidal expansion is under slight extension, and therefore sealing against the structures of the sides and the floor of the terminal rectum. Both effects, in combination, prevent the leaking of feces and fluid past the device, and facilitate the transport of the bowel contents through the anus. The irrigation volume is kept inside the rectum with this embodiment by the spontaneous tonus of the anus, resting on the trans-anal device portion, and causing the drainage lumen to be largely occluded. While the filling volume of the balloon can be chosen to cause a slight overpressure in the opening condition, the filling volume during the irrigation itself is kept on the same low level, as it is maintained in intervals between the bowel management procedures.

The filling volumes required to achieve the various seal and opening effects on the drainage lumen 13 are described in conjunction with a syringe-like filling aid, herein below.

Both device embodiments, with or without structurally connected tube segments 5 and 6, allow for continuous spontaneous defecation during the indwelling placement of the device. While the passage of feces through the trans-anal portion of the basic device is driven by the peristaltic contractions of the colon and rectum, and the trans-anal portion shows a passive opening of its drainage lumen 13, in the embodiment with inter-connected tube ends, the opening and unwinding of the lumen is supported actively, when sufficiently strong rectal contractions appear.

Alternative to the stiffening sleeve 14, which is made from a tube- or ring-like cylindrical structure, and is fixed in the inside of the central drainage lumen 13, as shown in FIG. 3A, the opening of the drainage lumen can be realized by a foam based element 106, which is positioned inside the space 10 of the everted balloon structure, as pictured in FIG. 3B. A foam element 106 can be fixed on the outer surface of the tube segment 6, e.g. by an adhesive. Its length, in the preferred case, is equivalent to the length of the lumen 13 in the everted toroidal device section. In other embodiments, as indicated in FIG. 3C, the foam element 106 can be elongated by a cylindrical extension 107 from the intra-rectal position into, or beyond, the trans-anal channel. In particular embodiments the extension 107 can be extended to, and fixed with, the connector element 9.

Figure 5:
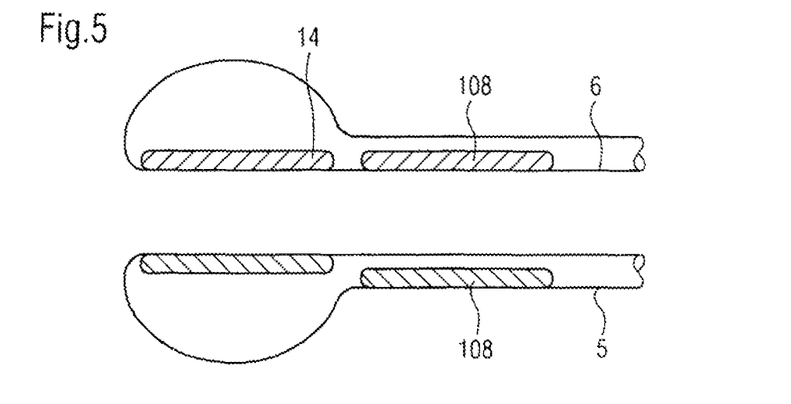
FIG. 5 is a schematic view showing a reinforcing elasticity modifying element in the trans-anal device portion of the present invention.

In order to modify and adjust the specific elasticity and/or re-erecting properties of the tube segments, which form the trans-anal device portion, the trans-anal tube segments 5 and 6 can be reinforced by attached additional tubing, or sleeve-like elements, from cast, injection molded, or foamed, or gel-based material. As shown in FIG. 5, reinforcing element(s) 108 can be fixed either on the outside or inside of the tube ends. In the preferred case, an element 108 is fixed on the outside of the tube 6, facing into the space 10 between the two concentric tube layers, thus being protected from the fecal material passing the drainage channel. The reinforcing elements can cover the surfaces of the tube segments, which are making the trans-anal portion of the device, partially or over their entire surface. An elasticity modifying and adjusting function can be further integrated into the trans-anal device portion by a spiral shaped element, or a web-like structure, of thin filament. Also, an according gel-like structure is plausible. As a special variation of the device, a gel based sleeve on the outward surface of the tube-like end segment 5 can reduce the irritating effect of the trans-anal device portion. Further, an enforcement with adjustable re-erecting properties can be created by a thin-walled, soft and flexible medium-filled tube, which is wrapped in a spiral around the tube ends, preferably around the outer surface of the tube-like end 5, facing to the inside of the space 10.

Figure 4A:
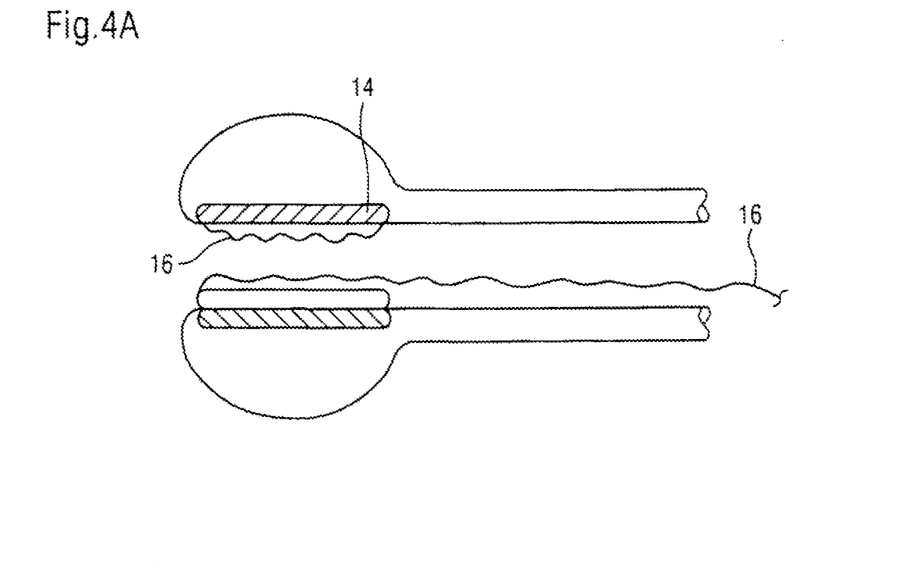
FIG. 4A is a schematic view of an embodiment of the present invention having a drainage lumen occluding balloon element, which is integrated into a stiffening sleeve.

In FIG. 4A the invention further describes embodiments of the device, whereby the blockage of the central drainage lumen 13 can be performed independently from the filling status of the tube/balloon 2 and the space 10. For that purpose, an occluding balloon 16 is provided. The balloon 16 is preferably disposed inside the stiffening sleeve 14, and is provided with a spherical preshape with a diameter that is preferably slightly greater than the inside diameter of the stiffening sleeve 14. The inflated occluding balloon 16 thereby completely seals the central drainage lumen 13 and bears in all circumferential directions against the inside of the stiffening sleeve 14, thereby sealing it. In other device versions, the sealing balloon can also be extended in length throughout the entire intra-rectal and trans-anal draining lumen 13.

Figure 4B:
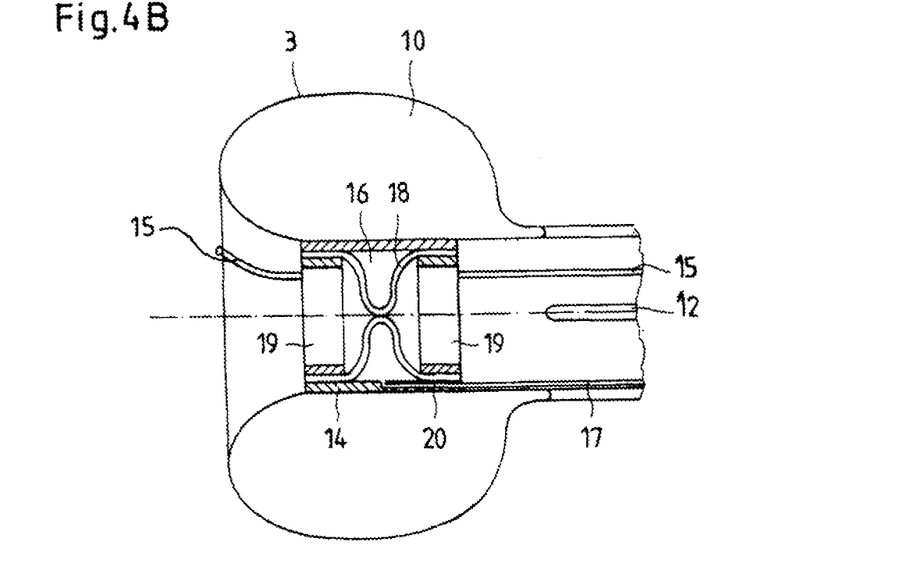
FIG. 4B shows an alternative embodiment of the present invention having an occluding balloon element.

As shown in FIG. 4B, opening into the occluding balloon 16 is an additional tube 17, by which a filling medium can be conducted into the balloon 16 from the outside. Roughly in a region where the tube 17 opens into the occluding balloon 16, the latter is affixed to the stiffening sleeve 14. Alternatively, the tube 17 can be fixed on the inside wall of the lumen 13, penetrating to the outside through a connector 19, or at a further proximal position within the connected draining tube portion.

The embodiment of FIG. 4B differs from the forgoing only in that the occluding balloon 16 is provided with a different configuration. In this embodiment, this element is configured as a short tube 18 having roughly the same diameter and length as the stiffening tube 14. The tube 18 can be preshaped in the form of a radial expansion in its axial middle segment. Both ends of the tube 18 are affixed to the inside of the stiffening sleeve 14, for example by being clamped between it and the respective connector 19 inserted in each end. The two connectors 19 can, in addition, be fixed in the stiffening sleeve 14 with glue and form a structural unit with it. If the hollow space between the medial unclamped region of the tube 18 and the stiffening sleeve 14 is filled with a fluid from the outside, the tube 18 buckles inward, as can be seen in FIG. 4B, and seals the drainage lumen 13 in the manner of an iris. For filling with a fluid, the stiffening sleeve 14 can be provided with a conduit 20 that passes all the way through it from the patient distal side to the region between the two connectors 19, where it feeds into the inside. The tube 17 communicates with a conduit 20. In an alternative embodiment, the inner connector 19, which is faced towards the anus, can be positioned at a further proximal position within the trans-anal portion of the draining channel, inside the connector 19 or inside the lumen of the proximal draining tube.

Alternative to preshaped balloons from blow-molded, thin-walled polyurethane, balloon 16 or short tube 18 can be made from compliant material, enabling an elastic distension of the balloon from a resting to a working state dimension. While the preshaped balloon allows to occlude the drainage lumen at small force, gradually increasable from ambient pressure to a desired pressure, the compliant balloon has to be distended under force to reach the occluding diameter, thus possibly exerting a force on the exposed structures, which is potentially traumatizing or impairing device function.

Figure 6:
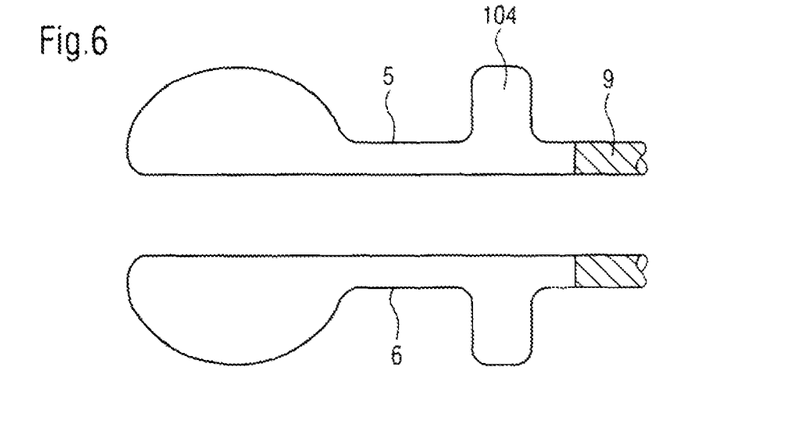
FIG. 6 is a schematic view showing a radial expansion in the pre-anal section of the trans-anal device portion of the present invention.

FIG. 6 shows an embodiment with an additional expansion, or expansions 109 in, the outer tube segment 5 of the trans-anal device portion. The expansions are preferably integrated in embodiments of the invention, which have a structural connection between the outer and inner tube-like ends 5 and 6. The expansions 4 or 109 are intended to serve as a counter-element to the balloon-shaped extension in the intra-rectal tube segment. Its function is to keep the device in a defined position and prevent the dislocation of the anchoring and sealing intra-rectal balloon segment into the colon. In an advantageous improvement of the invention, the outwardly directed pre-shape in the trans-anal region of the outer layer of the balloon has a ring or a disk shaped geometry. It is also possible for the outwardly oriented pre-shaped expansion 109 to include one or more fingers that diverge roughly diametrically from each other. These finger-like extensions can be placed in the anal fold to maximize wearing comfort. A wedge shaped element can further be provided, particularly fastened over the outer layer of the tube segment forming the balloon, in the trans-anal region or in the region of the transition from the trans-anal region to the connector element. A foam element of this kind can also serve as an abutment and additionally has increased rigidity, accompanied as a result by good positional stability.

Figure 7:
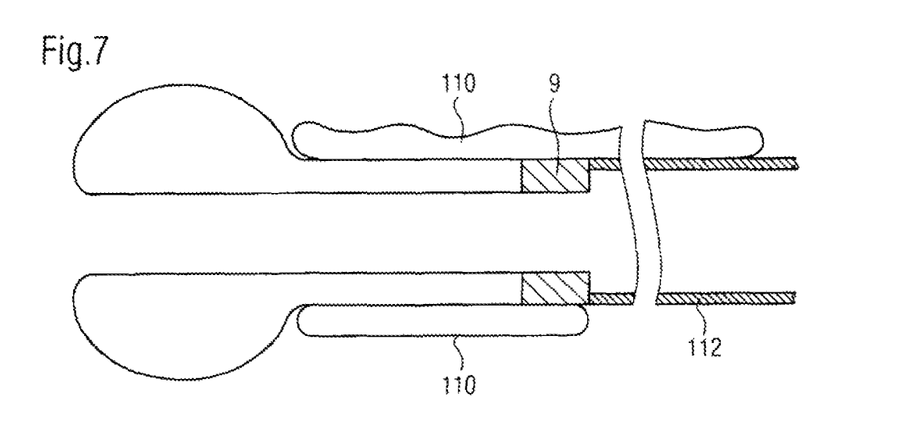
FIG. 7 is a schematic view showing an additional outer tube foil layer for mechanical decoupling of the trans-anal and further proximal device portions of the present invention from mucosa and body skin.

Another embodiment is shown in FIG. 7. In order to further improve the non-irritating properties of the device, a third tube foil layer 110 can be integrated, in order to mechanically decouple a trans-anal and proximally draining device 112 from the trans-anal mucosa and body skin. The tube foil is preferably made from very thin-walled foil extruded material with a thickness of about 5 to 30 µm, preferably 5 to 10 µm. Its diameter should exceed the outer diameter of the freely unfolded trans-anal and the proximal draining device portion by about 3 to 20 mm, preferably 5 to 10 mm. It can be made, for example, from polyurethane, soft PVC or an isoprene. In its preferred version, the outer layer 110 extends from the transition of the intra-rectal to trans-anal portion through the anus into the peri-anal portion of the device. In other embodiments, it can be extended about 50 cm in proximal direction, where it is fixed to the outer surface of the draining tube portion. The layer 110 reduces skin damage, possibly caused by sheer forces, which are effected by portions of the device that are otherwise directly resting on the skin or mucosa, as they may appear, when an axially and laterally acting pull force is applied on the device and device portions are accordingly stretched over the anal, gluteal or the upper limb skin. The created compartment between the protecting layer 110 and the inner device can be permanently opened to the outside by e.g. a perforation, can be completely sealed off from the outside, or can be equipped with an access for filling to adjust the filling volume individually.

The filling volume of the space 10 can be applied by a syringe device 111 bearing device function related filling markings.

Figure 8A:
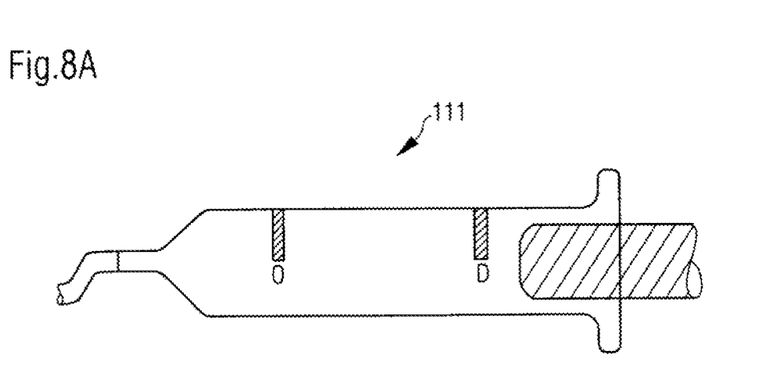
FIGS. 8A and 8B are schematic views showing filling syringes with volume markings.

FIG. 8A shows that by injecting a certain volume D (for drainage) into the basic device (without inter-connected tube segments as shown in FIG. 1B), the intra-rectal toroidal portion is unfolded roughly to its shape, added to that volume is roughly the volume that accords to those portions of the trans-anal portion of the space 10, that are not collapsed by the anus resting on it. By increasing the injected volume to the marking O (for occlusion), the intra-rectal outer segment end is cylindrically erected and fully collapsing the drainage lumen. Volume O accords the volume toroidal plus the volume of the cylindrically erected tube segment 5.

Figure 8B:
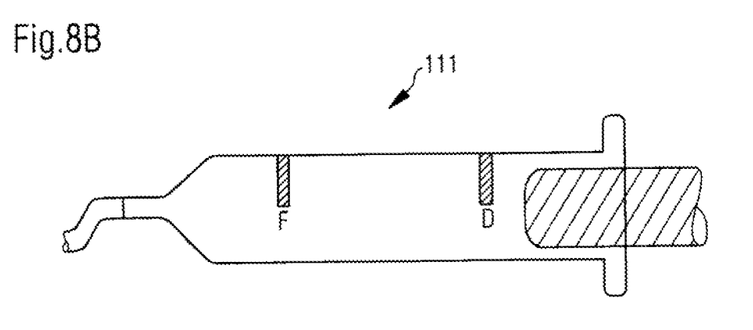

According to FIG. 8B, the device with inter-connected tube ends (as shown in FIG. 1C), is filled with a drainage volume D that roughly equals the toroidal volume plus the volume between the inter-connected trans-anal tube segments of the trans-anal device portion. In order to facilitate the removal of irrigation fluid and bowel contents through the drainage lumen, the filling volume can be increased to F (for flushing), bringing the intra-rectal toroid into a slightly extended state and causing an opening of the drainage lumen into the opening anal channel.

What is claimed is:

1. A device for sealing and draining a natural or artificial intestinal outlet, the device comprising an inflatable balloon with a generally toroidal structure, and formed of a flat, everted tube segment whose two ends extend generally coaxially one inside the other and are each connected with their ends to a sleeve, creating a sealed-off volume inside said balloon, whereby the filling of the sealed-off volume can be adjusted from outside of a body, and creating a draining lumen radially inside an inner layer of said balloon, an outer layer of the everted tube segment comprising a radially expanded intra-rectal device portion which is adapted to extend inside a rectum or an intestine of a patient during use, and comprising a trans-anal device portion narrowed with respect thereto, which is adapted to extend through an anus of the patient, or the patient's abdominal wall, during use, whereby a stiffening sleeve element is positioned inside the draining lumen of said intra-rectal device portion, keeping the draining lumen open and facilitating the uptake and passage of feces through an intra-rectal segment of the draining lumen, while two concentric tube layers of said trans-anal device portion, depending on a filling status of the sealed-off volume, can either be collapsed inside an anal channel to a small diameter, thereby forming a non-dilating structure, but allowing for free spontaneous passage of feces, or can unfold and erect inside the anal channel, thereby forming a trans-anally sealing structure with occluded draining lumen, wherein the stiffening sleeve element extends only inside the intra-rectal device portion and does not extend into said trans-anal device portion, and wherein said balloon is preshaped from thin-walled material with soft foil characteristics, exhibiting only limited compliance, allowing for tissue friendly non-irritating long-term placement and shape consistency under exertion of force, and wherein the material comprises a polyurethane having a shore hardness within a range of 80 A to 60 D, or a polymer with a similar hardness range.

2. The device according to claim 1, wherein both ends of the tube segment are adapted to be disposed outside the rectum, and outside the anus, and outside the abdominal wall.

3. The device according to claim 1, wherein said balloon is preshaped to, or beyond, working state dimensions thereof, as determined from intestine diameter.

4. The device according to claim 1, wherein the sealed-off volume inside said balloon is selected such that a wall of said balloon, when being placed and used inside the intestine and anus, is not stretched or distended by a filling volume equal or larger than the sealed-off volume of the balloon when being freely unfolded outside of the body to its full size, and therefore has a flaccid consistency.

5. The device according to claim 1, wherein pressure inside the sealed-off volume of said balloon, when being placed and used inside the intestine and anus, is adapted to be equal to pressure radially outside of said balloon, due to an unstretched state of said balloon.

6. The device according to claim 1, wherein pressure inside the sealed-off volume of said balloon, when being placed and used inside the intestine and anus, is adapted to be equal to an intrarectal pressure or equal to an intra-abdominal pressure of the patient.

7. The device according to claim 1, wherein said intra-rectal device portion of said outer layer of said everted balloon is provided with a thickness of 40 µm or less.

8. The device according to claim 1, wherein said intra-rectal device portion of said outer layer of said everted balloon is provided with a thickness of 15 µm or more.

9. The device according to claim 1, wherein a segment of said trans-anal device portion is provided with a thickness of 120 µm or less.

10. The device according to claim 1, wherein the tube segment of said trans-anal device portion is provided with a thickness of 30 µm or more.

11. The device according to claim 1, wherein the tube segment forming said trans-anal device portion is provided with a Shore hardness of greater than 80 A.

12. The device according to claim 11, wherein the stiffening sleeve element has a Shore hardness equal to, or smaller than, the Shore hardness of the tube segment forming said trans-anal device portion.

13. The device according to claim 1, wherein the stiffening, lumen-opening sleeve element is not connected to either end of the tube segment forming said balloon.

14. The device according to claim 1, wherein the stiffening sleeve element is integrated into the draining lumen of said intra-rectal device portion of said balloon, and is integrated into a radial expansion of the draining lumen.

15. The device according to claim 1, wherein the stiffening sleeve element is positioned inside an intra-rectal portion of the balloon on an outer side of the inner layer of said intra-rectal device portion of said balloon.

16. The device according to claim 1, wherein the stiffening sleeve element is of a soft polyurethane foam.

17. The device according to claim 1, wherein coaxially arranged tube segments, in said trans-anal device portion, are inter-connected.

18. The device according to claim 1, wherein an opening diameter of the draining lumen is regulated independently from outside by adjusting the filling status of the sealed-off volume of said balloon, in said trans-anal device portion, or of a separate lumen occluding and opening balloon element positioned inside the stiffening sleeve element.

19. The device according to claim 18, wherein the lumen occluding balloon element is seated inside the stiffening sleeve element or inside a further proximal portion of the draining lumen, and in said trans-anal device portion.

20. The device according to claim 19, wherein the lumen occluding balloon is formed from a thin-walled, preshaped material.

21. The device according to claim 20, wherein the lumen occluding balloon element is formed as a fully elastically restorable compartment radially inside said balloon, and inside the draining lumen.

22. The device according to claim 1, wherein a flushing, or irrigation, channel extends from a proximal portion of the device to a distal opening inside the rectum.

23. The device according to claim 1, wherein provided at the stiffening sleeve element, in the region of a distal rim thereof, is a flushing opening connected to a conduit that extends along the trans-anal device portion inside a drainage channel, and is adapted to introduce a flushing fluid.

24. The device according to claim 1, wherein the outer layer of said balloon comprises an outwardly oriented expansion of annular or disk-shaped geometry.

25. The device according to claim 24, wherein the medium filled into the sealed-off volume allows for drainage of bowel contents, or a change of volume occluding the drainage lumen, or facilitates flushing and free trans-anal passage of feces out of the patient.

26. The device according to claim 1, wherein the outer layer of said balloon comprises an outwardly oriented expansion comprising two fingers that diverge diametrically from each other.

27. The device according to claim 1, wherein said trans-anal device portion is coated at a radially outer face with a gel.

28. The device according to claim 1, wherein said trans-anal device portion is enclosed by a discrete continuous tube-like foil layer of a thinner material than the balloon material.

29. The device according to claim 1, wherein a medium filled into the sealed-off volume, is a liquid.

* * * * *